US 7,494,971 B2

(12) United States Patent
Eibl

(10) Patent No.: US 7,494,971 B2
(45) Date of Patent: *Feb. 24, 2009

(54) PHARMACEUTICAL PREPARATIONS AND MEDICINES CAPABLE OF GENERATING, AND/OR CONTAINING, THROMBIN

(75) Inventor: Johann Eibl, Vienna (AT)

(73) Assignee: Bio & Bio Licensing SA (LU)

( * ) Notice: Subject to any disclaimer, the term of this patent is extended or adjusted under 35 U.S.C. 154(b) by 126 days.

This patent is subject to a terminal disclaimer.

(21) Appl. No.: 11/041,165

(22) Filed: Jan. 21, 2005

(65) Prior Publication Data

US 2005/0192223 A1    Sep. 1, 2005

Related U.S. Application Data

(63) Continuation of application No. PCT/AT03/00208, filed on Jul. 23, 2003.

(30) Foreign Application Priority Data

Jul. 23, 2002 (AT) ............................. A 1113/2002
Jul. 21, 2003 (WO) ....................... PCT/AT03/00204

(51) Int. Cl.
 *A61K 38/36* (2006.01)
 *C07K 14/00* (2006.01)
(52) U.S. Cl. ............................. 514/2; 514/12; 435/214; 530/381
(58) Field of Classification Search .................... 514/12, 514/2; 435/214; 530/381
See application file for complete search history.

(56) References Cited

U.S. PATENT DOCUMENTS

| 4,160,025 A | 7/1979 | Eibl et al. |
| 4,188,318 A | 2/1980 | Shanbrom |
| 4,286,056 A | 8/1981 | Andary et al. |
| 4,395,396 A | 7/1983 | Eibl et al. |
| 6,358,534 B1 | 3/2002 | Schwarz et al. |

FOREIGN PATENT DOCUMENTS

| CA | 2156991 | 2/1996 |
| DE | 198 24 306 | 11/1999 |
| EP | 0 680 764 | 11/1995 |
| EP | 0 700 684 | 5/1996 |
| WO | 8102105 | 8/1981 |

OTHER PUBLICATIONS

Search Report for PCT/AT2003/000208 (translation).*
Butenas et al., "Normal" Thrombin Generation, Blood, 1999, 94:2169-2178.
Lämmle and Griffin, 1985, "Formation of the fibrin clot: the balance of procoagulant and inhibitory factors," Clinics in Haematology 14(2):281-342.

* cited by examiner

*Primary Examiner*—Chih-Min Kam
(74) *Attorney, Agent, or Firm*—Baker Botts L.L.P.

(57) ABSTRACT

The invention relates to a pharmaceutical active ingredient preparation for producing a medicament that contains thrombin or has a thrombin-generating capacity and compositions comprising thereof. The inventive preparation contains: (A) prothrombin obtained from plasma or by means of genetic engineering (coagulation factor II), (B) coagulation factors V, VIII, IX, X obtained from plasma or by means of genetic engineering, which can be at least partially in the activated state, and coagulation factor XIa obtained from plasma or by means of genetic engineering, and (C) phospholipids which are safe from prions and contribute to the clotting process, said phospholipids being optionally contained in liposomes.

27 Claims, No Drawings

PHARMACEUTICAL PREPARATIONS AND MEDICINES CAPABLE OF GENERATING, AND/OR CONTAINING, THROMBIN

CROSS REFERENCE TO RELATED APPLICATION(S)

The present application is a continuation of International Patent Application No. PCT/AT03/000208, filed Jul. 23, 2003, published in German on Feb. 5, 2004 as International Patent Publication No. WO04/011024, which claims priority to Austrian Application No. A 1113/2002, filed Jul. 23, 2002 and International Patent Application No. PCT/AT03/000204, filed Jul. 21, 2003, published as WO2004011023, all of which are incorporated herein in their entireties.

INTRODUCTION

The invention concerns a pharmaceutical preparation capable of generating, and containing, thrombin, and medicines manufactured thereof.

BACKGROUND OF THE INVENTION

When blood vessels are injured, blood escapes from the vascular space and coagulates. The injured blood vessels are closed by the coagulating blood and, in that manner, protect the organism from massive blood loss. Blood coagulation is caused by the enzyme thrombin, which is generated from its zymogen, prothrombin, and causes the transformation of the protein fibrinogen, which is present in blood plasma, into insoluble fibrin. The exiting blood coagulates within minutes, with only one sixth of the fibrinogen contained in plasma being transformed into fibrin. Thrombin generation continues in the coagulated blood, which still contains large amounts of fibrinogen, until all of the residual fibrinogen in the coagulated blood has been transformed into fibrin. This process of continued thrombin formation and coagulation proceeds slowly over a prolonged period of time and may take several hours until it is completed.

When fibrinogen is transformed into fibrin, thrombin causes fibrinopeptides A and B to split or partially split from the two ends of the fibrinogen molecule, whereby fibrin monomers are formed, which remain soluble for some time. These aggregate laterally to fibrils, forming a fibrin network in the further course (Blombäck). This fibrin network, which has formed in the coagulated blood, adheres to the injured tissue or wound bed and, in that manner, leads to hemostasis and wound closure.

Thrombin also causes the transformation of coagulation factor XIII, the zymogen of coagulation factor XIIIa, into a transglutaminase. The latter cross-links proteins such as fibrin, fibrin monomers, fibrinogen, and other proteins occurring in blood plasma by covalent bonds. The cross-linking of fibrin, in particular, is of great importance for the stability of the nascent fibrin network (Siebenlist et al.).

Thrombin also transforms the thrombin-activatable fibrinolysis inhibitor (TAFI) into a carboxypeptidase (TAFIa), which splits carboxyterminal lysine residues from fibrin and thereby inhibits the formation of the tissue-plasminogen-activator-plasminogen-fibrin-complex, which is necessary for the transformation of plasminogen into plasmin (Booth).

In vitro, the formation of thrombin in blood or blood plasma and thus the onset of the coagulation process is rendered possible by tissue extracts. Such extracts can best be obtained from brain using aqueous media or organic solvents (Morawitz).

The coagulation-active material, which can be extracted using a suitable buffer and which is termed thromboplastin, consists of an apoprotein, the tissue factor, and coagulation-active lipids. Small amounts of thromboplastin, when added to blood or plasma, suffice to generate rapid coagulation.

Using organic solvents, it is possible to separate the coagulation-active lipids from apoprotein. The aqueous apoprotein part is then termed partial thromboplastin, which, in the presence of kaolin, glass powder, and other surface-active substances also leads to rapid coagulation when blood or blood plasma are added.

This has led to the concept of an activation cascade of enzymes resulting in the formation of the enzyme thrombin, which causes blood coagulation (Davie et al.; MacFarlane).

The coagulation process which is triggered by thromboplastin is referred to as the extrinsic pathway of blood coagulation, in contrast to the coagulation process which is triggered by partial thromboplastin, the latter being termed the intrinsic pathway. The two processes have in common that they transform coagulation factor X into Xa, albeit by different routes. Accordingly, a differentiation is made between the extrinsic and intrinsic tenase pathways in the first part of the coagulation process, which leads to activation of coagulation factor X. In another enzyme complex, prothrombinase, coagulation factor Xa converts prothrombin into thrombin. This process is referred to as the common pathway. The enzyme system which generates coagulation factor Xa with the aid of thromboplastin is termed the extrinsic tenase complex, in contrast to the enzyme system in which partial thromboplastin plays a role, i.e. the intrinsic tenase complex.

The prevailing view has it that tissue factor, jointly with coagulation factor VIIa and thrombocytes trigger blood coagulation after injuries (Rapaport et al.). Tissue factor occurs in almost all tissues in very varying amounts along with coagulation-active lipids, and the two substances, when in contact with blood, form the extrinsic tenase complex, since small amounts of activated coagulation factor VII are always present in blood (Drake et al.). The extrinsic tenase complex transforms both, coagulation factors X and IX into Xa and IXa, respectively, and IXa transforms X into Xa. The activation of factor X and the resulting formation of thrombin, however, come to a halt rapidly by the tissue factor pathway inhibitor (TFPI). The temporarily formed extrinsic tenase complex as well as coagulation factor XIa independently lead to the activation of the intrinsic tenase complex, which, as far as the activation of coagulation factor X is concerned, is 50-fold more active than the extrinsic tenase complex. The intrinsic tenase complex consists of activated coagulation factors IXa, VIIIa, and coagulation-active phospholipids and is not inhibited by TFPI (von dem Borne et al.). In the intrinsic pathway, the activity of the enzyme coagulation factor IXa, which transforms coagulation factor X in Xa, is increased 100,000 to 1,000,000-fold. This increase is caused by cofactor VIIIa, which itself is not an enzyme, and certain phospholipids at an optimum calcium ion concentration.

Since the intrinsic tenase complex transforms coagulation factor X into Xa very rapidly, and the latter, jointly with cofactor Va and coagulation-active phospholipids, activates prothrombin, great amounts of thrombin are formed in a very short time. (Mann et al.).

The individual coagulation factors and platelets—the essential components of blood responsible for the process of coagulation—are normally present in abundance. Only if one of these components is reduced by 90% or more, an increased propensity to bleeding can be noticed. Bleedings become life-threatening only in deficiency states where a coagulation factor and/or platelets drop to several percent of their normal values. The central importance of tissue factor in triggering the coagulation process and its dissemination in all organs is beyond doubt, however, severe disturbances of blood coagulation occur in tissues with low tissue factor content in cases where a factor of the intrinsic tenase complex or of the prothrombinase complex is pathologically reduced. A case in point are patients suffering from hemophilia A or B. The blood of these patients still coagulates in most instances, however, because the intrinsic tenase complex is deficient or absent, thrombin formation in the coagulated blood is insufficient and the clot dissolves rapidly, so that no satisfactory hemostasis is achieved.

Thrombin, mostly of bovine origin, is used as a medicinal product for non-parenteral administration to achieve hemostasis in cases of superficial injuries. Its hemostyptic effect could be improved decisively when administered jointly with medicinal products containing fibrinogen (Grey; Young et al.). Because of their species-specific use, fibrinogen and thrombin are obtained primarily from allogenic source material today. By combining the application of thrombin with fibrinogen-containing medicinal products, one attempts to mimick and improve the physiological blood coagulation and accompanying hemostasis. This can be achieved also in patients with severe blood coagulation disturbances (Matras et al.).

By combining the application of fibrinogen concentrates, whose fibrinogen content amounts to 10- to 20-fold the fibrinogen content of blood, and great amounts of thrombin (100-1000 U per mL), it is possible to reduce the coagulation time in such a fibrinogen-thrombin mixture to a matter of seconds and obtain a 10 to 100-fold reduction compared to the physiological bleeding time. This has made it possible to practically achieve instantaneous hemostasis when such fibrinogen-thrombin mixtures are applied in an optimal manner, provided that no larger blood vessels, particularly arterial vessels, were injured (Spängler).

The fibrinogen transformed into fibrin by thrombin adheres to the wound bed as does coagulated blood, the transglutaminases which were activated by the action of thrombin obviously causing covalent bonds between the injured tissue and the fibrin formed. This strong adherence of the formed fibrin to tissue can be used also to glue non-bleeding tissue, since the formed fibrin does not impair the healing of the glued tissue in most cases and is largely degraded in a matter of days or weeks (Matras et al.).

When fibrinogen-thrombin mixtures are used to achieve hemostasis, an as rapid as possible initiation of the coagulation process is desirable. In contrast, a gradual onset of the coagulation process is preferable in cases where parts of tissue are glued and also for sealing purposes. This makes it possible for the tissue parts to be adapted more appropriately, and similar adaptations are necessary in sealing. Thus far, a slowing of the coagulation process has been achieved by a reduction of the thrombin concentration to approximately 1% of the amount of thrombin used to achieve hemostasis. However, the use of both, high and low concentrations of thrombin is accompanied by disadvantages.

Highly viscous fibrinogen solutions containing between 5 and 10% fibrinogen can be brought to coagulate with thrombin amounts ranging from 100 to 1000 units within seconds. This short coagulation time is necessary to achieve hemostasis rapidly after the application of such a mixture to a bleeding site and arrest the bleeding. The disadvantage of such a procedure is that the fibrinogen and thrombin solutions are poorly mixed, since the high viscosity of the mixture does not allow satisfactory mixing in a short time. What results is a non-homogenous coagulation with an attendant impairment in biomechanical quality.

On the other hand, if fibrinogen-thrombin mixtures are used not to achieve hemostasis but rather to glue parts of tissue, it is necessary in most cases to slow down the coagulation of the fibrinogen-thrombin mixture in order to be able to optimize the adaptation of the parts to be glued or sealed before coagulation occurs. At present, this is attempted by reducing the amount of thrombin to between one tenth to one hundredth of the amount of thrombin used to achieve hemostasis at the disadvantage that not all of the fibrinogen present is converted into fibrin and not all of the factor XIII is converted to factor XIIIa. This procedure is also not suitable for obtaining an optimal fibrin clot, since the low thrombin concentration is not sufficient to transform TAFI into TAFIa.

A further problem is the use of bovine materials for the manufacture of medicinal products containing thrombin. Since a risk of transmission of prions by any bovine organs cannot be excluded with certainty, bovine thrombin is hardly used anymore today.

Bovine thrombin has the further disadvantage that it is antigenic for other species and can provoke allergies and anaphylaxes. In addition, patients treated with bovine thrombins have been observed to develop coagulation disorders, which is attributable to the fact that bovine thrombin can cause the formation of antibodies against coagulation factors which cross-react with human coagulation factors, thus retarding the coagulation process.

In manufacturing thrombin from prothrombin, thromboplastin from animal source material, mostly bovine brain, has often been used to activate thrombin, which increases the yield. Because of the risk of transmission of prions, thromboplastin from bovine source is rarely used anymore in the manufacture of thrombin, and a poor thrombin yield is put up with instead.

SUMMARY OF THE INVENTION

The invention relates to a pharmaceutical active ingredient preparation for producing a medicament that contains thrombin or has a thrombin-generating capacity and compositions comprising thereof. The inventive preparation contains: (A) prothrombin obtained from plasma or by means of genetic engineering (coagulation factor II), (B) coagulation factors V, VIII, IX, X obtained from plasma or by means of genetic engineering, which can be at least partially in the activated state, and coagulation factor XIa obtained from plasma or by means of genetic engineering, and (C) phospholipids which are safe from prions and contribute to the clotting process, said phospholipids being optionally contained in liposomes.

DETAILED DESCRIPTION OF THE INVENTION

The subject invention aims inter alia at making available a virally safe pharmaceutical preparation which is capable of generating thrombin and which, when formulated into a medicinal product capable of generating thrombin and when mixed with a pharmaceutical preparation containing fibrinogen, gives a complete and homogenous mixture of the two components, without too rapid a coagulation process preventing complete mixing. The aim, however, is not only to render possible complete mixing, but also the adaptation of tissue parts to be glued or sealed before coagulation begins. Thrombin generation must continue also after the onset of coagulation in order to convert all of the fibrinogen, factor XIII, and TAFI into fibrin, factor XIIIa, and TAFIa, respectively, so that the wound closure obtained by fibrin be durable, and in which the prothrombin it contains is converted as completely as possible into thrombin and the latter can be further purified and used for the manufacture of a medicinal product containing thrombin. This medicinal product can be used as such or jointly with other medicinal products containing fibrinogen.

The medicinal products manufactured from the pharmaceutical preparations capable of generating thrombin should contain the allogenic material of the species to which they are intended to be applied only. Likewise, only species-specific proteins should be used in their manufacture. All source and auxilliary materials used should exclude a risk of transmission of prions. The generation of thrombin from prothrombin in vivo and in vitro should be as complete as possible, since it is only the prothrombin present in an already formed fibrinogen clot from which thrombin can be generated.

The pharmaceutical preparation or substance according to the invention is suitable for the manufacture of a medicinal product containing, or capable of, generating thrombin and is characterized in that it contains:
  (A) prothrombin obtained from plasma or by recombinant technology (coagulation factor II),
  (B) coagulation factors V, VIII, IX, X obtained from plasma or by recombinant technology, which may be present at least partly in activated form, and plasmatic or recombinant coagulation factor XIa, and
  (C) prion-safe, coagulation-active phospholipids, which may be incorporated in liposomes.

The pharmaceutical preparation according to the invention contains preferably coagulation factor VII obtained from plasma or by recombinant technology or a mixture of plasmatic or recombinant coagulation factors VII and VIIa. In addition, it contains preferably a recombinant tissue factor as such or in relipidated form.

The pharmaceutical preparation according to the invention may also consist of two or more plasma fractions and the coagulation active phospholipids, the individual plasma fraction containing one or more coagulation factors and/or activated coagulation factors of components (A) and (B). The whole plasma fraction mixture must, however, contain all coagulation factors and/or activated coagulation factors contained in components (A) and (B), tissue factor preferably being added.

The coagulation factors, in particular, are manufactured exclusively from the blood plasma of a particular mammalian species or the corresponding recombinant coagulation factors or activated coagulation factors, including tissue factor.

In the pharmaceutical preparation according to the invention, prothrombin, coagulation factors V, VIII, IX, X, XIa, and coagulation factors VII and VIIa, if present, as well as tissue factor are preferably rendered virally safe by virus inactivation and/or virus partitioning.

The pharmaceutical preparation according to the invention may be present in deep-frozen or freeze-dried form.

The invention also concerns a medicinal product capable of generating thrombin which can be manufactured from a pharmaceutical preparation according to the invention.

The medicinal product capable of generating thrombin according to the invention may be present in deep-frozen or in freeze-dried form.

A preferred embodiment of the medicinal product capable of generating thrombin according to the invention is characterized in that it contains thrombin in such amounts that it will contain no more than 1 U of thrombin per mL after thawing or reconstitution.

The invention also concerns a medicinal product containing thrombin and which can be manufactured from a pharmaceutical preparation capable of generating thrombin according to the invention. It may be provided in deep-frozen or freeze-dried state.

The invention also concerns a medicinal product mixture which coagulates within 30 to 300 seconds by mixing a medicinal product according to the invention with a medicinal product containing fibrinogen prior to application.

The invention also concerns a medicinal product containing thrombin which, if mixed with the medicinal product mixture described above will coagulate within 3 to 10 seconds.

A preferred method for the manufacture of a pharmaceutical preparation containing thrombin according to the invention is characterized in that a pharmaceutical preparation capable of generating thrombin according to the invention is mixed with Ca-ions, which results in a product containing thrombin and which is subsequently purified by chromatography.

A preferred embodiment of the process according to the invention is that the pharmaceutical preparation is rendered virally safe by subjecting it to virus inactivation during or after thrombin generation and to virus removal after thrombin generation is complete.

The invention also concerns a process for the manufacture of a pro-cofactor-concentrate containing coagulation factors V and VIII and which is characterized in that plasmatic cryoprecipitate is dissolved and fibrinogen is separated from the solution, whereby a solution is obtained which contains coagulation factors V and VIII and which can be mixed with calcium chloride.

Another process according to the invention concerns the manufacture of a prothrombin complex concentrate containing coagulation factor XI in addition to coagulation factors II, VII, VIIa, IX, X, and XI, and containing per 1.0 μg prothrombin at least 0.030 μg coagulation factor XIa and which is characterized in that plasmatic cryoprecipitate supernatant is adsorbed onto an anion exchanger and a prothrombin complex containing coagulation factor XIa is eluted after washing the adsorbate and storage in the cold.

The invention is based on the finding that a virally safe intrinsic tenase-prothrombinase-complex is responsible for a next-to-complete, timewise controllable formation of α-thrombin from virally safe prothrombin. The intrinsic tenase-prothrombinase-complex is generated by activation of the respective coagulation factors, which either are or have been rendered virally safe, in the presence of optimal Ca-ion-concentrations, with prion-safe, coagulation-active phospholipids and the virally safe activator substance coagulation factor XIa and/or the virally safe activator substances coagulation factors VIIa and tissue factor.

Thus, the aims of the present invention are accomplished by a pharmaceutical preparation, consisting of three components (Components A, B, and C), for the manufacture of a virally safe medicinal product capable of generating, or containing, thrombin, the pharmaceutical preparation being characterized in that Component A contains virally safe prothrombin obtained from plasma or genetically engineered, as a pharmaceutical active substance, Component B contains virally safe, plasma derived or genetically engineered coagulation factors V, VIII, IX, X, XIa as pharmaceutical active substances and, in case the generation of extrinsic tenase complex is desirable in addition to the generation of prothrombinase and intrinsic tenase complexes, also contains virally safe coagulation factors VII and/or VIIa as well as tissue factor as pharmaceutical active substances, and Component C contains fully synthetic, coagulation-active phospholipids as pharmaceutical active substances having a transformation point of the paracrystalline into the liquid-crystalline form at beyond 15° C. A mixture of the pharmaceutical active substances, i.e. the coagulation factors and/or activated coagulation factors contained in Components A and B can also be obtained by mixing two or more plasma fractions containing all necessary pharmaceutical active substances and to which tissue factor has been added, if necessary.

After mixing of the three components and addition of an optimum amount of $CaCl_2$, thrombin is generated temperature-dependent between 0° and 40° C., the rate of thrombin generation increasing with rising temperatures.

Component A is manufactured by dissolution of freeze-dried, virally safe prothrombin or thawing of a frozen solution of virally safe prothrombin and preparation of a prothrombin stock solution containing 10-100 units of prothrombin per mL and 0.1% sodium citrate at pH 7.3.

Potency of the stock solution is assessed by determination of the prothrombin units using coagulation factor-II-deficient plasma, and establishing a calibration curve using a reference normal plasma.

With the aid of ecarin, the maximum amount of meizothrombin/thrombin is determined which can be generated from one unit of prothrombin. The meizothrombin/thrombin determination is carried out with chromogenic substrate S-2238. In addition, the amount of thrombin in NIH units is determined which is generated from one unit of prothrombin after the addition of thromboplastin. A corresponding standard curve for the determination of thrombin is generated using the international α-thrombin standard.

Component B is manufactured by mixing stock solutions of virally safe coagulation factors V, VIII, IX, X, XIa as well as coagulation factors VII, VIIa, and tissue factor. The concentrations of the individual coagulation factors in their stock solutions lie between 10 and 100 units per mL; the tissue factor stock solution contains 25 µg/mL. Instead of a stock solution of coagulation factor V, a stock solution of coagulation factor Va may be used. The content of an individual coagulation factor in a stock solution is determined using the corresponding deficient plasmas, and a standard curve with pooled normal plasma is established to determine each individual coagulation factor.

In order to determine what amounts of the individual coagulation factors are necessary to still obtain an optimum thrombin generation, different mixtures of Components A and B are prepared, containing one unit each of coagulation factors II, V, VIII, IX, X, XIa, and II, XIa, VII, VIIa, and 2.5 µg tissue factor, respectively, per mL of sample. After addition of the liposome emulsion and subsequent recalcification, thrombin generation is determined at 26° C. at different time intervals. In the samples, prothrombin consumption and the generation of β- and y-thrombin are also determined. Prothrombin is transferred into thrombin in the presence of 0.1% PEG and the amounts of coagulation factors and tissue factor per mL are determined which are necessary to still achieve an optimum thrombin generation.

Mixtures of Components A and B may also be obtained from two or more plasma fractions to the extent they contain as pharmaceutical active substances all coagulation factors and activated coagulation factors necessary for the generation of the intrinsic tenase and prothrombinase complexes. The intrinsic tenase pathway is activated either by coagulation factor XIa or via the extrinsic tenase pathway, particularly when TFPI is absent. It is also possible to activate the intrinsic tenase pathway by coagulation factor XIa and via the extrinsic tenase pathway simultaneously. In the presence of coagulation factor XIa, or by its addition to, a mixture of coagulation factors which are necessary for the generation of the intrinsic tenase complex, it is also possible to determine whether or not at least 90% of the prothrombin in the mixture have been transferred into thrombin, and if that is not the case, what amounts of factor VIIa and tissue factor are necessary to achieve a complete transfer of prothrombin into thrombin. A surplus of coagulation-active phospholipids is used to generate thrombin. The activation is carried out at 26° C. or 37° C. and at an optimum Ca-ion concentration.

The coagulation factors used and/or the plasma fractions containing the coagulation factors as well as the genetically engineered tissue factor are rendered virally safe by virus inactivation, e.g. the solvent/detergent method, and subsequent virus removal by nanofiltration.

Component C is manufactured from mixtures of fully synthetic, and therefore, prion-safe, choline- or serinephospholipids or from choline-serine-ethanolamin-phospholipids. Only phospholipids are used which transfer from the paracrystalline gel state into the liquid-crystalline state between 15° and 40° C. From the phospholipid mixtures, emulsions can be produced which contain liposomes having diameters ranging from 20 nm to 1000 nm and which have the polar parts of the phospholipids in an outer membrane. Using temperatures between 50° and 100° C., liposomes can be produced having diameters of 20 nm-200 nm. Such emulsions can be sterilized using bacterial-tight filters, sterile filled, dried, and stored under nitrogen. The freeze-dried emulsions can be reconstituted with water.

The coagulation factors used and the non-relipidated tissue factor can be rendered virally safe by virus inactivation, preferably the solvent/detergent method and subsequent removal of the solvent/detergent. Quantifiable traces of the solvent used, tri-n-butylphosphate, and of the detergent, Tween 80, remain in the thrombin-containing solution. Virus removal is achieved preferably by nanofiltration after prior clarifying filtration using a series of filters with narrowing pores, decreasing from 5000 nm to 35 nm. Preferably, after filtration through a 35 nm filter, also nanofilters with pore sizes of 20 nm and 15 nm may be used.

Thrombin generation of this pharmaceutical preparation is highly temperature dependent. Therefore, it is possible to inhibit the formation of thrombin from prothrombin in mixtures of Components A, B, and C, even at optimum Ca-ion concentration, if low temperatures around freezing-point are used in processing. The pharmaceutical preparation according to the invention can be deep-frozen for storage or can be freeze-dried and stored between 0° and 25° C.

The pharmaceutical preparation capable of generating thrombin can be formulated at low temperatures into a medicinal product having a thrombin generation capacity of preferably 100 to 1000 units of thrombin per mL, sterile filtered, portioned, and filled.

The pharmaceutical preparation capable of generating thrombin is also used for the manufacture of thrombin-containing medicinal products. Thrombin generation is preferably carried out at temperatures ranging between 20° and 40° C.

For the manufacture of thrombin from a pharmaceutical preparation capable of generating thrombin containing one or more components that have not been virus inactivated, virus inactivation can be carried out during or after thrombin generation. The virus inactivating substances can be removed in the course of the subsequent purification of the generated thrombin. It is possible to obtain a thrombin-containing pharmaceutical substance having a thrombin content of 1000 to 10000 units per mL, which is subjected to virus removal by clarifying filtrations and subsequent nanofiltration. The virally safe substance can then be formulated, sterile filtered, and processed into a medicinal product.

Medicinal products capable of generating, and/or containing, thrombin can be used in combination with fibrinogen-containing medicinal products to achieve hemostasis, to glue sutured tissue, and seal body cavities and vessels against leakage of gasses and body fluids.

By mixing a medicinal product capable of generating thrombin with a fibrinogen-containing medicinal product and addition, if any, of low amounts of thrombin, the coagulation time of such a mixture can be adjusted to 30 to 300 seconds. In that manner, complete mixing of the medicinal products in such a mixture is possible, even if the viscosity is high. Also, after complete mixing of the medicinal products, enough time remains for the necessary adaptation of the tissue parts that need to be glued or sealed. Once coagulation sets in—similarly to the physiological coagulation process—more thrombin is generated in the partly coagulated fibrinogen, so that after some time—up to several hours—practically all prothrombin has converted into thrombin and the latter transforms all of the fibrinogen into fibrin. Such a continued thrombin generation renders possible not only the homogenous generation of fibrin in the already coagulated fibrinogen, but also the uniform activation of factor XIII and subsequent onset of the cross-linking of the generated fibrin, as well as the activation of TAFI and the subsequent splitting-off of the end-terminal lysine residues of fibrin.

The application of fibrinogen-containing mixtures for hemostasis requires a very short coagulation time. In order to achieve this, and at the same time guarantee a homogenous formation of the coagulated fibrinogen and the activation of zymogens such as factor XIII and/or TAFI, fibrinogen-containing medicinal products can be mixed completely with medicinal products capable of generating thrombin, and such mixtures can be applied to the bleeding site jointly with a thrombin solution having a high thrombin content. Although the onsetting coagulation does not immediately lead to a homogenous fibrin clot, the generation of thrombin in the fibrin clot continues as the thrombin-generating medicinal product contained in the clot continues to transform prothrombin into thrombin, resulting in a homogenous coagulated fibrin clot with homogenously distributed factor XIIIa and homogenously distributed TAFIa. This makes it possible to achieve an excellent fibrin structure and high resistance against fibrinolytic influences even with rapidly coagulating mixtures of thrombin-containing and fibrinogen-containing medicinal products.

Another possibility to trigger spontaneous thrombin generation in a mixture of coagulation factors capable of generating thrombin which consists of prothrombin complex and factor VIII is by addition of factors of the contact system. For that purpose, coagulation factors XI and XII need to be added, unless they are already contained in the mixture.

The activation of coagulation factor XI in vivo as yet is not understood in all detail. What is known is that blood cells and cells of the endothelium play an important role in this activation process. In blood, factor XI is bound to high molecular kininogen ($K_d 10^{-8}$) and prothrombin ($K_d 10^{-7}$) in non-covalent form. These complexes may accumulate on activated platelets, this leading to activation of coagulation factor XI if thrombin and/or coagulation factor XIIa are present.

In vitro, coagulation factor XI can be activated by coagulation factor XIIa on negatively charged surfaces, coagulation factor XIIa being generated from coagulation factor XII by kallikrein. The formation of kallikrein from prekallikrein present in blood can occur by different mechanisms, such as by prekallikrein activator or metal salts of ellagic acid.

According to the invention, thrombin can be generated spontaneously in a mixture of coagulation factors capable of generating thrombin and consisting of prothrombin complex and coagulation factor VIII, by activation of the coagulation factor XI contained therein, all components of the mixture having been virus inactivated. Preferably, this activation is performed in the presence of prion-safe, coagulation-active phospholipids with virally safe kallikrein. Instead of kallikrein, also virally inactivated prekallikrein with virally inactivated prekallikrein activator or prekallikrein activators can be used, such as metal salts of ellagic acid.

For the manufacture of thrombin-containing pharmaceutical substances, virus inactivation can also be performed during or after thrombin generation.

The following examples describe the invention in greater detail.

EXAMPLES

Preparation of Component A.

100 mg of virally inactivated prothrombin are dissolved in 1 L of 0.1% sodium citrate solution at pH 7.5, and the prothrombin content per mL is determined using prothrombin-deficient plasma. After the addition of ecarin, the generated amounts of meizothrombin and thrombin are determined by splitting of chromogenic substrate S-2238. In addition, thrombin generation is determined using a prothrombinase preparation. The generated thrombin is determined with the aid of a fibrinogen solution as thrombin time. With this fibrinogen solution, a standard curve was previously established using the international standard for α-thrombin. This prothrombin stock solution can be deep-frozen at −20° C. and stored for at least six months.

Preparation of Component B from Individual Coagulation Factors.

Virally safe, highly purified coagulation. factor concentrates manufactured from plasma or obtained by genetic engineering are dissolved in 0.1% sodium citrate pH 7.5 and mixed under stirring: 3.2 mg of factor V, 0.2 mg of factor VIII, 5.0 mg of factor IX, 11 mg of factor X, and 0.5 mg of factor XIa. After sampling, the solution is deep-frozen and stored at −20° C. or temperatures below that. An equivalent sample is used to determine the amount of a 1M $CaCl_2$-solution which is necessary to adjust the Ca-ion-activity to 5 mM -8 mM.

Preparation of a Mixture of Components A and B.

The frozen solutions of Component A, prepared according to Example 1, and Component B, prepared according to Example 2, are carefully thawed. Care must be taken for the temperature not to rise above 4° C. From the solutions thus obtained, a mixture of equal parts of Components A and B is prepared, the necessary samples are drawn, and the mixture of the two Components is again frozen and stored at −20° C.

Preparation of a Mixture of Plasma Fractions Containing the Coagulation Factors of Components A and B.

From 10 L of deep-frozen Source Plasma that has been carefully thawed at a temperature not exceeding 4° C., the cryoprecipitate is separated from the cryo- supernatant by centrifugation at 6000 g for 15 minutes.

Prothrombin Complex Concentrate Containing Coagulation Factor XIa:

The cryo-supernatant is mixed with 16 g of weak anion exchanger DEAE-Sephadex A-50, the pH is adjusted to between 7.8 and 8.8 using 0.1 normal sodium hydroxide, and the mixture is stirred at a temperature of between 3° and 6° C. for one hour. The mixture can be kept at this temperature until the ion exchanger is separated by filtration and/or centrifugation, which must be accomplished within no more than 24 hours. The liquid released from the ion exchanger is stored for preparation of other plasma fractions, and the separated ion exchanger is used for the manufacture of prothrombin complex. The ion exchanger obtained in the manner described can be stored at a temperature of between 4° and 6° C. for up to 100 hours. For further processing, the separated ion exchanger is washed twice, each time with 1 L of 0.5% saline, and the prothrombin-complex-containing coagulation factor XIa is obtained by elution of the ion exchanger with 1000 mL of a 0.3 NaCL solution at pH 7.5. After elution, the ion exchanger is washed with 500 ml of a 0.3 M NaCl solution at pH 7.5 once more, and the rinse is added to the eluate. Using ecarin, the amount of prothrombin present in the total eluate is determined, and the total eluate is adjusted by dilution to the desired prothrombin content, which may lie between 2 and 5 prothrombin units per mL. The total eluate, which is coagulation factor-XIa-containing prothrombin complex concentrate, may be frozen and stored at −20° C. Using samples drawn before freezing, the contents of coagulation factors and activated coagulation factors are determined.

Preparation of a Pro-cofactor Concentrate:

The cryoprecipitate sedimented from plasma by centrifugation is dissolved in 750 mL of 0.3% citrate buffer pH 7.0 and mixed with 110 g glycine. After stirring at a temperature of between 0° and 2° C. for one hour, the precipitated fibrinogen is separated by centrifugation at 3000 g for 15 minutes, and the supernatant, which contains coagulation factors V and VIII, is frozen. In a sample of the supernatant which has been diluted with water at a ratio of 1:10, the content of factor VIII is determined, as well as the amount of $CaCl_2$ which is necessary for recalcification, in order to obtain an ion activity equivalent to that of a 5 mM $CaCl_2$ solution. The frozen solution can be stored at −20° C.

Preparation of a Mixture of Coagulation-factor-XIa-containing Prothrombin Concentrate and Pro-cofactor Concentrate:

A recalcified sample of pro-cofactor concentrate prepared according to Example 4b. which has been diluted with distilled water 1:10, is added to prothrombin concentrate prepared according to Example 4a. in amounts of 0.1, 0.2, 0.4, and 0.8 mL per mL of prothrombin concentrate. To each of these mixtures, 0.1 mL of a liposome emulsion prepared according to Example 5 is added. After incubation at 26° C. for eight hours, the amount of pro-cofactor concentrate is determined which is necessary to transfer 90% or more of the prothrombin present into thrombin.

For the preparation of the mixture from prothrombin complex concentrate containing coagulation factor XIa, and pro-cofactor concentrate which have been obtained from 10 L of deep-frozen plasma and have been stored frozen, these concentrates are thawed and mixed at the optimum ratio previously determined. The mixture is frozen and stored at −20° C.

Manufacture of Component C without Emulgator.

Fully synthetic, and therefore, virally and prion-safe phospholipids are used. 200 mg 2Na-1,2-di-oleoyl-sn-glycero-3-phospho-L-serine, 400 mg 1,2,di-oleoyl-sn-glycero-3-phosphocholine, and 400 mg di-oleoyl-ethanolamine-phospholipid are dissolved in 10 mL chloroform, and the solution is evaporated in a 250-mL round-bottomed flask by heating and continuous rotation until most of the chloroform is removed. Residual chloroform is removed by a nitrogen stream, and 10 mL of 0.1% citrate buffer solution pH 7.3 are added. The phospholipid film on the inner wall of the round-bottomed flask is completely emulsified in the buffer solution at 65° C. During emulsification, the flask is repeatedly shaken in a Vortex device until the lipid film has completely disappeared. The emulsion as such or diluted 1:10 with 0.1% citrate buffer pH 7.0, is filtered through a filter having a pore size of 0.45 μm and is subsequently sterile filtered through a 0.22 μm filter. This liposome emulsion can be stored sterile in a refrigerator and is shaken in a Vortex device for 1 minute prior to use. The emulsion is tested for sterility and pyrogenicity according to the European Pharmacopoeia (Eur.Pharm.$4^{th}$ Edition 2002, pages 123-126, 2.6.1. Sterility. Pages 131-132, 2.6.8. Pyrogens).

Preparation of Component C using Sodium Cholate.

250 mg 2Na-1,2-di-oleoyl-sn-glycero-3-phospho-L-serine, 750 mg 1,2,di-oleoyl-sn-glycero-3-phosphocholine and 500 mg sodium cholate are dissolved in 10 mL of a 1+1 mixture of chloroform and methyl alcohol, and the two solvents are evaporated under vacuum so that a thin, uniform film settles on the inner wall of a round-bottomed flask. The film is washed off with 10 mL 0.1% citrate buffer pH 7.3, and the emulsion obtained in that manner is processed and sterile filtered as described in Example 5.

Virally safe activator substances for the activation of the intrinsic tenase pathway.

Coagulation factor XIa alone or in combination with coagulation factor XI, or coagulation factor VIIa, preferably with tissue factor, are used as activator substances. Coagulation factor XIa can also be used jointly with coagulation factor VIIa and tissue factor. For use as pharmaceutical active substances, the activated coagulation factors and tissue factor are virus inactivated by a solvent/detergent method, and after removal of the solvent/detergent, are subjected to virus partitioning by nanofiltration.

The following pharmaceutical active substances, dissolved in 0.3% citrate buffer pH 7.3, are used as stock solutions of the activator substances:

30 μg factor XIa/mL;
30 μg factor XIa and 50 ng factor XI/mL;
30 μg factor XIa and 20 ng factor VIIa/mL;
30 μg factor XIa and 20 ng factor VIIa and 10 ng tissue factor/mL;
10 μg/mL tissue factor.

For the purpose of determining the best suitable activator substance, 10 μL each of a dilution series of the individual activator substances are added to 1 mL each of the coagulation factor mixtures prepared according to Examples 3 or 4 and are mixed with a 10 μL of a 1:100 dilution of a liposome emulsion prepared according to Example 5. After recalcification, the mixtures are kept at 26° or 37° C. The amount of factor Xa generated is determined using chromogenic substrate S-2251 at intervals of 10, 30, 60, and 120 min. The activator substance which generates the greatest amount of factor Xa from the coagulation factor concentrates produced according to Examples 3 and 4 after recalcification, is used for the manufacture of a pharmaceutical substance capable of generating thrombin.

Determination of the amounts of Component C necessary to transform at least 90% of the prothrombin present in a mixture of Components A and B at 26° C. within eight hours or 37° C. within two hours.

Coagulation factor mixtures according to Examples 3 or 4, to which activator substances in amounts determined according to Example 7 may have been added, are mixed with increasing amounts of liposome emulsions. To 10 mL-samples of each coagulation factor mixture, 0.1, 0.2, 0.4, or 0.8 mL of a 1:100 dilution of a liposome emulsion produced according to Example 5 are added after recalcification, the mixtures are incubated for eight hours at 26° or two hours at 37° C. The minimum amount of liposome emulsion is determined which is necessary to transform at least 90% of the prothrombin present into thrombin.

Preparation of a virally safe pharmaceutical substance capable of generating thrombin.

A virally safe coagulation factor mixture produced according to Example 3 (Components A and B) is thawed, if necessary mixed with an appropriate amount of a virally safe activator substance selected as described in Example 7, and the mixture is stirred at 0° to 2° C. for 15 minutes. To the mixture, the amount of liposome emulsion (Component C) determined in Example 5 is added. The mixture is adjusted to a concentration of 0.9% NaCl using solid sodium chloride, subjected to clarifying filtration, and sterile filtered through 0.22 μm and/or 0.1 μm filters. The whole manipulation, including sterile filtration, is carried out at a temperature between 0° and 2° C. The pharmaceutical substance capable of generating thrombin obtained in that manner is sampled, frozen, and stored at −20° C. The necessary tests for stability and pyrogenicity are carried out according the European Pharmacopoeia. The capacity of generating thrombin is determined in in-process controls and in the sterile filtrate after recalcification at 37° C. over two hours, along with residual amounts of prothrombin which can be activated by ecarin, in order to guarantee an at least 90% conversion of prothrombin into thrombin.

Preparation of a Virally Safe Pharmaceutical Preparation Containing Thrombin.

The frozen mixture produced from a factor-XIa-containing prothrombin complex concentrate and a pro-cofactor concentrate according to Example 4 is thawed, and, if desirable after Example 7, mixed with a selected, calculated amount of activator substance. By addition of 10 mg Tween 80 and 0.3 mg tri-n-butylphosphate per g protein of the coagulation factor mixture at 26° C. after recalcification and addition of the amount of liposome emulsion determined according to Example 6, the major amount of the prothrombin is converted into thrombin within eight hours, and virus inactivation is carried out at the same time.

The thrombin-containing solution can be either frozen and stored or be used immediately or after thawing. By the addition of sodium citrate solution, the Ca-ion concentration is adjusted to 25 mM and the pH to 6.5. Under continued stirring at room temperature, polyethylene glycol having a molecular weight of between 6000 and 8000 is added in an amount to achieve a 0.1% solution. A 20% CM-sepharose suspension that has been washed with 0.025 M sodium citrate pH 6.5 is then added under stirring until at least 95% of the available thrombin has been adsorbed onto the CM- sepharose. The required amount of CM-sepharose is determined previously by estimating the lowest amount of the 20% emulsion which adsorbs at least 95% of the available thrombin. The CM-sepharose is centrifuged off between 3000 and 5000 g for 30 minutes, the sediment is resuspended in 25 mM citrate buffer pH 6.5 and filled into an appropriate column. The column is washed at pH 6.5 with 1% citrate buffer containing also 0.1% PEG and eluted with a sodium chloride gradient in the presence of 0.1% citrate and 0.1% PEG at pH 6.5. The sodium chloride gradient is established between 10 and 200 mM. The fractions containing most of the thrombin are collected, diafiltered, the concentration being thereby adjusted to approximately 500 U thrombin per mL. Such a solution can be frozen, stored after freeze-drying or further processed without delay.

After clarifying filtration by filters of different pore sizes ranging from 5000 nm to 75 nm, the thrombin-containing solution is filtered through a 35 nm-nanofilter and preferably through further nanofilters having pore sizes of 20 nm and 15 nm. The virally partitioned thrombin solution obtained in that manner is concentrated to a content of more than 5000 U thrombin per mL using a 30 KD-filter, frozen or freeze-dried, and stored.

Preparation of a Virally Safe Medicinal Product Capable of Generating Thrombin.

An equivalent sample of the virally safe pharmaceutical substance that has been produced according to Example 9 and has been frozen or freeze-dried, is diluted with a 0.9% NaCl solution in a manner to ensure it will generate 500±50 U thrombin per mL after recalcification at 37° C. within two hours.

Such a diluted sample is mixed with an equal amount of a 5-10% fibrinogen-containing medicinal product which is planned to form part of a fibrin sealant kit, and the coagulation time of this mixture is determined after recalcification. If the coagulation time at 37° C. exceeds 150 seconds, the pharmaceutical substance according to Example 7 is admixed with an amount of thrombin produced as described in Example 8 appropriate to lower the coagulation time to between 100 and 150 seconds.

The amounts of thrombin determined in that manner are added to the substance obtained as described in Example 9 under stirring at a temperature of between 0° and 2° C., and the mixture is clarified by filtration and sterile filtered. The resulting sterile bulk solution is portioned and filled into final containers, preferably at the same temperature, and is freeze-dried. The freeze-dried powder is reconstituted with a sterile 5 mM calcium chloride solution.

Preparation of a Virally Safe Medicinal Product Containing Thrombin.

A pharmaceutical substance according to Example 10 is thawed or reconstituted and adjusted to a concentration of 0.9% NaCl using sodium chloride. Isotonic saline is added to adjust the thrombin concentration to between 500 and 5000 U per mL, as desired. PEG is added in an amount to produce a 0.1% solution, and a 10% $CaCl_2$ solution is added in an amount to obtain a 5 mM $CaCl_2$ solution. This solution is sterile filtered, portioned and filled into final containers under sterile conditions. It can be frozen or freeze-dried for storage. Freeze-dried thrombin solution is reconstituted with Water for Injections.

Use of a Medicinal Product Capable of Generating Thrombin in Combination with a Medicinal Product Containing Thrombin.

1 mL of fibrinogen-containing medicinal product containing 50-100 mg fibrinogen per mL is mixed with 1 mL of a medicinal product capable of generating thrombin according to Example 11. The mixture of the two medicinal products is stirred under sterile conditions for approximately 20 seconds, and the homogenous mixture obtained in that manner is applied to tissues to be glued or sealed after they have been adapted to their desired positions. The glued or sealed tissues are held in the adjusted positions until the mixture of the two medicinal products has coagulated. If necessary, they may be arrested in the fixed position for a longer period of time, even for several hours.

Use of a Medicinal Product Containing Thrombin.

To 2.0 mL of a mixture of medicinal products according to Example 13, 0.2 mL of a medicinal product containing thrombin according to Example 12 at a concentration of 2000 u thrombin/mL are added and mixed rapidly. To achieve hemostasis, this mixture is applied to bleeding sites without delay, preferably after accumulated blood has been removed by sucking, swabbing or blowing it off.

Determination of coagulation factor XI and of coagulation factor XII in ion-exchanger eluates according to Example 4a which are not stored after charging but eluted immediately after washing of the charged ion exchanger.

Determination is Carried out using Coagulation-Factor-Deficient Plasmas by American Diagnostica.

Determination of kallikrein and prekallikrein in eluates of ion exchangers which are charged with prothrombin complexes and are eluted immediately after washing or only after storage for up to 100 hours at refrigerator temperature.

Kallikrein activity is determined using chromogenic substrate S-2403. A 4 mM chromogenic substrate solution is used, which gives a final concentration of 0.4 mM. The prekallikrein concentration is also determined with chromogenic substrate S-2403, a 1:100 dilution of the eluate being mixed with an equal volume of a 0.5% kaolin suspension and incubated at 37° C. under stirring for five minutes. Prior to the measured extinction, the extinction which is obtained without activation of the kaolin suspension is deducted, and the amounts or units prekallikrein are determined using a standard curve.

Determination of Prekallikrein Activator.

Prekallikrein activator determination is performed in the same manner as the determination of prekallikrein, except that a concentration series of prekallikrein activators is used instead of kaolin suspensions. If copper salts of ellagic acid are used, a concentration series of between 10 ng and 10000 ng is used, which generates the maximum amount of kallikrein from a prekallikrein sample at 37° C. within five minutes.

Preparation of plant and/or or synthetic phospolipid emulsions from L-α-phosphatidylcholine, L-α-phosphatidyl-L-serine, and L-α-phosphatidyl-ethanolamine, which is the same as described in Example 5.

Determination of TAFIa.

TAFIa is determined using chromogenic TAFI activity kits by American Diagnostica without the addition of activator (thrombin). The content of TAFIa is calculated from a standard curve, which was established using dilutions of plasma and subsequent activation with thrombin and measurement of the TAFIa- activity with a chromogenic substrate.

Determination of Coagulation Factor XIIIa.

Determination of activated factor XIII is carried out according to European Pharmacopoeia Suppl. 4.5. 07/2003, p.3687 without the use of activators of factor XIII (thrombin).

Ultrasound Treatment of Phospholipid Emulsions.

From the phospholipid mixtures, 1% suspensions are produced by dilution with isotonic saline, and 2 mL are subjected to ultrasonic irradiation. Ultrasonic irradiation is carried out with Ultrasound Desintegrator Sonifire II W-250. The output is a maximum of 200 watts at a frequency of 20 kHz. Konverter 102 C was used with standard resonator ½" and microtip 101-148-062. Ultrasonic irradiation is carried out for between 10 and 100 seconds without cooling of the irradiated emulsion at step 1 and at 10% pulsating interval. The activity of the irradiated phospholipid emulsion is determined by assessment of the partial thromboplastin time using a reference plasma and a kaolin suspension. 100 µL of plasma are incubated with 50 µL of a liposome emulsion and 50 µL of a 0.5% kaolin suspension at 37° C. for five minutes, recalcified, and the coagulation time at 37° C. is determined. The required amount of liposome emulsion is determined which causes the shortest coagulation time. The activities of the liposome emulsions described in Examples 5 and 6, and of the phospholipid emulsions according to Example 18 can be determined by this method.

Determination of the appropriate Ca-ion concentration for the desired adjustment of the coagulation time of a pharmaceutical substance capable of generating thrombin.

Pharmaceutical preparations generating thrombin are produced, and a geometric dilution series of the pharmaceutical preparation to be tested is mixed with Ca-ions, the highest Ca-ion concentration being 1 mM. The dilution series ranges from 125 µM to 1000 µM. Similarly, a Ca-ion concentration series is prepared ranging from 10 mM to 640 mM, and the coagulation time is determined. The required Ca-ion concentration is determined using a standard curve.

In a chessboard sample, the optimum mixture of a phospholipid mixture with kaolin is determined which, under optimum ultrasonic irradiation, shows the highest activity in APTT with plasma. The test is carried out using 100 µL of the irradiated mixture, which has been incubated with 100 µL of plasma at 37° C. for 5 minutes, and which is recalcified by addition of 100 µL of a $CaCl_2$-solution. To determine the optimum irradiation intensity, ultrasonic irradiation is carried out as described in Example 21, an 80% pulsating interval being used in steps 1, 2, and 3, and the samples being irradiated for 10, 30, 100, or 300 seconds.

BIBLIOGRAPHY

Blombäck B. Fibrinogen: Evolution of the Structure-Function Concept: Keynote Address at Fibrinogen 2000 Congress. Annals N.Y. Acad. Sci. 2001;936:1-10

Booth N. A. TAFI Meets the Sticky Ends. Thromb. Haemost. 2001;85:1-2

Davie E. W., Ratnoff O. D. Waterfall sequence for intrinsic blood clotting. Science 1964;145:1310-12

Drake T. A., Morrissey J. H., Edgington T. S. Selective cellular expression of tissue factor in human tissue. Implication for disorders of hemostasis and thrombosis. Am. J. Path. 1989; 134:1087-97

Grey E. G. Fibrin as a haemostatic in cerebral surgery. Surg. Gyn. Obst. 1915;21:452-454

MacFarlane R. G. An enzyme cascade in the blood clotting mechanism and its function as a biochemical amplifier. Nature 1964;202:498-9

Mann K. G., Jenny R. J., Krishnaswamy. Cofactor proteins in the assembly and expression of blood clotting enzyme complexes. Ann. Rev. Biochem. 1988;57:915-56.

Matras H. et. Al. Zur Klebung von Nervenanastomosen mit Gerinnungssubstanzen. Fortschr. Kiefer-Gesichts-Chir. 1976;112-114

Morawitz P. Die Chemie der Blutgerinnung. Ergebn. d. Physiol. 1905;4:307

Rapaport S. I., Rao L. V. M. The Tissue Factor Pathway: How it has become a "Prima Ballerina". Thromb. Haemost. 1995;74:7-17

Siebenlist K. R., Meh D. A., Mosesson M. W. Protransglutaminase (F-XIII) mediated cross-linking of fibrinogen and fibrin. Thromb. Haemost. 2001;86:1221-8

Spängler H. P. Gewebeklebung und lokale Blutstillung mit Fibrinogen, Thrombin und Blutgerinnungsfaktor XIII (Experimentelle Untersuchungen und klinische Erfahrungen). Wien. klin. Wschr. 1976;88(4):3-18

Von dem Borne P. A. K., Koppelman S. J., Bouma B. N. et al. Surface independent factor XI activation by thrombin in the presence of high molecular weight kininogen. Thromb. Haemost. 1994;72:397-402

Young F. et al. "Suture" of Wounds by Plasma-Thrombin Adhesion. War Med. 1944;6:80-85

The invention claimed is:

1. A pharmaceutical composition comprising:
   (A) an isolated prothrombin (coagulation factor II),
   (B) isolated virus-safe coagulation factors V, VIII, IX, X, and XIa, and
   (C) prion-safe, coagulation-active phospholipids wherein the coagulation factors are present in amounts capable of together generating thrombin.

2. The pharmaceutical composition according to claim 1 further comprising coagulation factor VII or a mixture of coagulation factors VII and VIIa.

3. The pharmaceutical composition according to claim 1, further comprising a genetically engineered tissue factor as such or in relipidated form.

4. The pharmaceutical composition according to claim 1 wherein the coagulation factors are produced exclusively from the blood plasma, from an allogenic sources, or from the corresponding genetically engineered coagulation factors or activated coagulation factors.

5. The pharmaceutical composition according to claim 1 wherein prothrombin, coagulation factors V, VIII, IX, X, XIa, and, when present, coagulation factors VII and VIIa, as well as tissue factor have been rendered virally safe by virus inactivation and/or virus partitioning.

6. The pharmaceutical composition according to claim 1 which is in deep-frozen or freeze-dried form.

7. A medicinal product capable of generating thrombin comprising the pharmaceutical preparation according to claim 1.

8. The medicinal product according to claim 7 which is in deep-frozen or in freeze-dried form.

9. The medicinal product according to claim 7 which further comprises thrombin in an amount to yield no more than 1 U of thrombin per mL after thawing or reconstitution.

10. The medicinal product of claim 7, wherein the medicinal product coagulates within 30 to 300 seconds when the medicinal product is mixed with a fibrinogen-containing product prior to application, whereby thrombin is generated.

11. The medicinal product of claim 10 wherein the prion-safe, coagulation-active phospholipids are from plant origin or plant and synthetic origin, in a ratio of phosphatidylcholines to phosphatidylserines of 3 to 1, or of phosphatidylcholines to phosphatidylserines to phosphatidylethanolamines of 2 to 2 to 1.

12. The medicinal product of claim 11, wherein the phospholipid is prepared by mixing with kaolin and irradiating with ultrasound, for use in activating prothrombin complex-containing solutions.

13. The medicinal product of claim 7, wherein the medicinal product coagulates within 3 to 10 seconds when the medicinal product is mixed with a fibrinogen-containing product prior to application, whereby thrombin is generated.

14. The medicinal product according to claim 7, wherein the comprised phospholipids are prepared using a phospholipid emulsion which has been subjected to ultrasonic irradiation.

15. The medicinal product according to claim 14, where the emulsion is further subjected to sterile filtration.

16. The medicinal product according to claim 15, wherein the phospholipid is prepared by mixing with kaolin and irradiating with ultrasound, for use in activating prothrombin complex-containing solutions.

17. The medicinal product according to claim 14, wherein the phospholipid is prepared by mixing with kaolin and irradiating with ultrasound, for use in activating prothrombin complex-containing solutions.

18. The medicinal product according to claim 7, prepared using an effective calcium ion concentration ranging from 10 mM to 640 mM.

19. A medicinal product containing thrombin comprising the pharmaceutical preparation according to claim 1.

20. The medicinal product according to claim 19 which is in deep-frozen or freeze-dried form.

21. The pharmaceutical composition according to claim 1, wherein coagulation factor XIa is generated from coagulation factor XI by coagulation factor XIIa on negatively charged surfaces, and wherein coagulation factor XIIa is generated from coagulation factor XII by the addition of virally inactivated or virally safe kallikrein, or virally inactivated or virally safe prekallikrein with virally safe prekallikrein activators.

22. The pharmaceutical composition according to claim 1 which further comprises thrombin-activatable fibrinolysis inhibitor or thrombin-activatable fibrinolysis inhibitor and coagulation factor XIII in addition to prothrombin complexes and which, after activation of prothrombin, contains at least 3 U (50 µg) activated thrombin-activatable fibrinolysis inhibitor or 3 U activated thrombin-activatable fibrinolysis inhibitor and 5 U coagulation factor XIIIa per 1000 U thrombin.

23. The pharmaceutical composition according to claim 1 comprising prion-safe, coagulation-active phospholipids from plant origin or plant and synthetic origin, in a ratio of phosphatidylcholines to phosphatidylserines of 3 to 1, or of phosphatidyl-cholines to phosphatidylserines to phosphatidylethanolamines of 2 to 2 to 1.

24. The pharmaceutical composition according to claim 1, wherein the comprised phospholipids are prepared using a phospholipid emulsion which has been subjected to ultrasonic irradiation.

25. The pharmaceutical composition according to claim 24, where the emulsion is further subjected to sterile filtration.

26. The pharmaceutical composition according to claim 25, wherein the phospholipid is prepared by mixing with kaolin and irradiating with ultrasound, for use in activating prothrombin complex-containing solutions.

27. The pharmaceutical composition according to claim 24, wherein the phospholipid is prepared by mixing with kaolin and irradiating with ultrasound, for use in activating prothrombin complex-containing solutions.

* * * * *